United States Patent [19]

Coleman et al.

[11] 4,048,302

[45] Sept. 13, 1977

[54] AQUEOUS PESTICIDAL SOLUTIONS CONTAINING POLYETHYLENE GLYCOL

[75] Inventors: William R. Coleman, Miami; Thomas E. Duffey, Hialeah, both of Fla.

[73] Assignee: Riviana Foods Inc., Houston, Tex.

[21] Appl. No.: 476,061

[22] Filed: June 3, 1974

[51] Int. Cl.$^2$ ............................................. A61K 31/74
[52] U.S. Cl. ........................................ 424/78; 424/300
[58] Field of Search .................................. 424/78, 300

[56] References Cited

U.S. PATENT DOCUMENTS

| 3,111,539 | 11/1963 | Bocker et al. ................. 424/300 X |
| 3,803,303 | 4/1974 | McKibben et al. ...................... 424/78 |

FOREIGN PATENT DOCUMENTS

| 7,243,822 | 11/1972 | Japan ..................................... 424/78 |
| 1,234,126 | 6/1971 | United Kingdom .................. 424/78 |

OTHER PUBLICATIONS

Merck Index, 1968, 8th Ed., pp. 1095.
Carbowax Union Carbide Chemicals Co., 6/1960, pp. 11.

*Primary Examiner*—Dale R. Ore
*Attorney, Agent, or Firm*—Fidelman, Wolffe & Waldron

[57] ABSTRACT

Pesticides such as o-isopropoxyphenyl methylcarbamate are dissolved in polyethylene glycol. The concentrate thus formed is freely soluble in water.

3 Claims, No Drawings

AQUEOUS PESTICIDAL SOLUTIONS CONTAINING POLYETHYLENE GLYCOL

The present invention relates to a composition and method for treating domesticated animals for the control of ticks and fleas. More particularly it relates to pesticidal formulations and applications involving solutions of pesticides in aqueous media. Still more particularly, it relates to aqueous pesticidal solutions which readily wet and penetrate through the coat of domesticated animals and which readily wet the skin to kill parasitic infestations of ticks, fleas, and the like. More particularly yet, it relates to aqueous pesticidal solutions which can safely be used on a wide variety of mammals without transport of the pesticide through the skin and have consequent reduced levels of toxicity. It also relates to pesticidal compositions which avoid the use of irritating or toxic solvents, wetting agents, surfactants, and the like.

A wide variety of pesticidal formulations are known, used, and commercially available for use on domesticated mammals for killing or ridding the animal of parasites such as fleas, ticks, and the like. A rather large number of pesticides are used in such fashion and a wide variety of carrier media are employed.

The most common media are liquids, suitable for spraying, pouring, diping, brushing, wiping, and the like fashion of applications to the animals. Since the pesticides of interest are insoluble in water, or soluble only to such a slight degree as to be substantially insoluble, it is usual practice to dissolve the pesticidal component in an organic solvent, and to add a wetting agent or surfactant to the formulation. For use, the solution is diluted with a convenient quantity of water wherein, by virtue of the surfactant, an oil-in-water emulsion is formed, and the emulsion is applied to the animal to be treated.

Such pesticide emulsions present a number of disadvantages both to the animal and to the person using the formulation. Most of the organic solvents employed for such purposes, including most commonly xylene, toluene, methylated naphthalenes, petroleum oils such as kerosene, and the like, have objectionable odors. Some are noxious in character or may even be toxic. Such characteristics are undesirable both for the user and for the animal upon which such formulations are used. Some such solvents also can cause skin transport of the active pesticide which precludes use on many animals, particularly cats and kittens, and represents a potentially grave hazard for the user.

The use of surfactants lead to the deposit of a film on the coat of the animal which can prove unsightly and can also be objectionably sticky. The costs of surfactants is objectionably high as well.

It is readily apparent that an aqueous solution of a suitable pesticidal component would eliminate the worst of these problems and would prove highly desirable as a consequence. It is accordingly an object of the present invention to provide aqueous solutions of pesticides and a pesticide composition freely dilutable with water to form aqueous solutions.

It has now been found that many useful pesticidal compounds not soluble in water or soluble to such a limited extent as to be effectively insoluble can be placed in an aqueous solution by the solvating effect or polyethylene glycols. When formed in accord with the present invention, such pesticides are rendered soluble in water and form clear, water white solutions which are stable and which can effectively be applied to animals by any convenient conventional technique.

The pesticides to which the present invention is applicable includes all those which are soluble to an appreciable degree in polyethylene glycols. The pesticide of choice is o-isopropoxyphenyl methylcarbamate, which is disclosed more fully in U.S. Pat. No. 3,111,539, and which is an article of commerce available as "Bay 9010" from Chemagro Corporation of Kansas City, Missouri and has the structural formula:

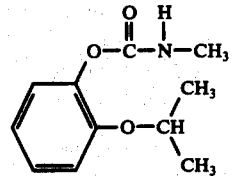

The polyethylene glycols contemplated in the present invention are the water soluble polymers having molecular weights ranging from about 200 up to as much as about 10,000. Such materials are well and widely known and are generally available in commerce, for example, as "Carbowax" from Union Carbide. These materials are polymers of ethylene oxide having the general formula:

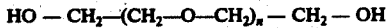

where n represents the average number of oxyethylene units in the polymer.

Polyethylene glycols having molecular weights of about 200 to 600 are clear, viscous liquids at ambient temperatures. At higher molecular weights up to about 10,000 the polymers are soft, white, waxy solids at ambient temperatures, but melt at relatively low temperatures, in the range of about 40° to 65° C, depending upon molecular weight.

In the present invention the polyethylene glycols in the molecular weight range of 200 to 600 are preferred, and 400 is most preferred. This is because solubility of the pesticide in the polymer and solubility of the polymer in water gradually decrease and viscosity of aqueous solutions increases. The lower molecular weight species are also more rapidly dissolved in water.

Proportions are not narrowly critical or significant to the present invention. For guidance of those of ordinary skill in the art, however, the following comments are offered as guidance in the practice of the present invention:

As a water dilutable concentrate, it is desirable to formulate the pesticide in solution in the polyethylene glycol in proportions on the order of about 5 to 15, preferably about 8 to 10, weight percent pesticide, with the balance polyethylene glycol. In such circumstance, a dilution with water of about one ounce per quart of water gives a generally desirable pesticide concentration for use, although the water may be about 10 to 50 times the weight of the concentrate if convenient. In more precise terms it is preferred that the pesticide be present in the diluted formulation at levels of about 0.125 to about 0.250 weight percent, particularly for use on cats or immature animals, such as puppies, kittens, or the like.

The preparation of the formulations is preferably, as suggested above, first as a concentrate of pesticide dissolved in the polyethylene glycol. Such concentrates are storage stable, convenient to package, inexpensive to transport, and can be readily diluted by the user by simple mixing with water. The concentrate is desirably formed by heating the polyethylene glycol to about 140° F., adding the pesticide, and mixing. Heat is not required but accelerates solution of the pesticide and is accordingly preferred.

In diluted form, the viscosity of the solution is low and application may be by any of the conventional techniques. The clear colorless solution readily wets the animals coat and skin and upon drying leaves no visible or tangible residue. On extremely long haired animals, such as collie dogs and the like, it may be helpful to rub or brush the coat to aid penetration, but with shorted haired animals, such procedures are not ordinarily necessary.

The formulations in accordance with the present invention have been found effective with domesticated mammals generally, and particularly with pets, such as cats and dogs, and with other animals such as horses, cattle, swine, sheep, goats, and the like. The particular pesticide investigated is effective against fleas, ticks, lice, mites, and cattle face fly and horn fly.

Formulation and use of the compositions of the present invention is illustrated by the following specific examples which represent the best mode of practicing the invention, but is not intended to be limiting upon the scope of the application but rather is presented only as illustrative guidance for those of ordinary skill in the art.

EXAMPLE I

One-hundred-eighty-four grams of a polyethylene glycol having a molecular weight of about 400 (Carbowax 400, Union Carbide) were placed in a 1 liter beaker and heated to about 140° F. Sixteen grams of o-isopropoxyphenyl methylcarbamate (Bay 9010, Chemagro Corporation) were added and the mixture stirred until a clear, colorless solution was formed, about ten minutes. The solution was poured into small 8 ounce polyethylene containers, capped, and allowed to cool. The result was a fluid, clear, colorless solution, having no detectable odor.

One ounce of the foregoing solution was added to one quart of water and stirred. The result was a fluid, clear, colorless solution, having no detectable odor.

Several flea infested dogs were sprayed with the aqueous solution. After thirty minutes, large numbers of dead fleas had dropped from the dogs. After two hours, the dogs were found substantially free of live fleas. After one week the dogs were again checked and no live fleas were found. Control dogs sprayed with a solution of one ounce polyethylene glycol (Carbowax 400) in one quart water remained infested.

EXAMPLE II

The formulation of Example I was tested for safety and efficacy with young kittens. The concentrate was diluted at 0.5, 1.0, 1.5, 2.0 and 4.0 ounces per quart of water and was employed as a dip.

Nineteen kittens, ranging in age from six to ten weeks were immersed, except for the head, in a bath of the formulation and placed in individual cages. Complete effectiveness against fleas was observed as in Example I at all dilutions.

The kittens were maintained under observation for side effects and adverse reactions over a period of three weeks. Surprisingly, no side effects were noted. At the end of the observations, the kittens remained free of fleas.

In view of the general sensitivity of cats and particularly kittens, the safety and absence of side effects is particularly surprising.

What is claimed:

1. An aqueous pesticidal solution for the treatment of the skin and costs of domesticated animals to kill fleas, ticks, lice, mites, cattle face flies and hornflies consisting essentially of a solution of about 5 to 15 weight percent of o-isopropoxyphenyl methycarbamate and about 95 to 85 weight percent polyethylene glycol having a molecular weight of about 200 to 600 dissolved in about 10 to 50 parts by weight water per part of the combined weights of said o-isopropoxyphenyl methylcarbamate and said polyethylene glycol.

2. The composition of claim 1 wherein said polyethylene glycol has a molecular weight of about 400.

3. The composition of claim 1 wherein said o-isopropoxyphenyl methylcarbamate is first dissolved in said polyethylene glycol and the concentrate solution thus formed is diluted in a ratio of about one ounce of said concentrate to a quart of water.

* * * * *

UNITED STATES PATENT AND TRADEMARK OFFICE
CERTIFICATE OF CORRECTION

PATENT NO. : 4,048,302
DATED : 9/13/77
INVENTOR(S) : William R. Coleman et al

It is certified that error appears in the above-identified patent and that said Letters Patent are hereby corrected as shown below:

In Column 4, line 30, "Costs" should read --coats--.

In Column 4, line 33, "methycarbamate" should read --methylcarbamate--.

Signed and Sealed this

Seventh Day of February 1978

[SEAL]

Attest:

RUTH C. MASON
*Attesting Officer*

LUTRELLE F. PARKER
*Acting Commissioner of Patents and Trademarks*